United States Patent
Malinin et al.

(10) Patent No.: US 9,610,143 B2
(45) Date of Patent: Apr. 4, 2017

(54) COMPRESSED DECALCIFIED TRABECULAR BONE GRAFTS AND TOOTH SOCKET REPAIR

(71) Applicants: Theodore Malinin, Miami, FL (US); Arun K. Garg, Miami, FL (US)

(72) Inventors: Theodore Malinin, Miami, FL (US); Arun K. Garg, Miami, FL (US)

(73) Assignee: Osteolife Biomedical, LLC, Miami, FL (US)

( * ) Notice: Subject to any disclaimer, the term of this patent is extended or adjusted under 35 U.S.C. 154(b) by 0 days.

(21) Appl. No.: 14/309,572

(22) Filed: Jun. 19, 2014

(65) Prior Publication Data

US 2015/0366641 A1 Dec. 24, 2015

(51) Int. Cl.
| | | |
|---|---|---|
| *A61C 8/00* | (2006.01) | |
| *A61C 8/02* | (2006.01) | |
| *A61C 13/00* | (2006.01) | |
| *A61C 13/08* | (2006.01) | |
| *A61F 2/28* | (2006.01) | |

(52) U.S. Cl.
CPC .......... *A61C 8/0012* (2013.01); *A61C 8/0006* (2013.01); *A61C 8/0089* (2013.01); *A61C 13/0004* (2013.01); *A61C 13/081* (2013.01); *A61F 2/28* (2013.01); *A61C 8/0018* (2013.01)

(58) Field of Classification Search
CPC .. A61F 2/28; A61F 2002/2835; A61C 8/0012; A61C 8/0006; A61C 8/0089; A61C 8/0018; A61C 13/0004; A61C 13/081
USPC .............. 433/215, 222.1, 229; 424/422–423; 623/16.11
See application file for complete search history.

(56) References Cited

U.S. PATENT DOCUMENTS

| | | | | |
|---|---|---|---|---|
| 4,277,238 A | * | 7/1981 | Katagiri | A61C 8/0012 422/36 |
| 4,725,234 A | * | 2/1988 | Ethridge | ........................ 433/215 |
| 4,851,046 A | * | 7/1989 | Low et al. | ....................... 106/35 |
| 5,112,354 A | | 5/1992 | Sires | |
| 5,866,155 A | * | 2/1999 | Laurencin et al. | ........... 424/425 |
| 6,293,970 B1 | * | 9/2001 | Wolfinbarger et al. | ..... 623/23.61 |
| 6,325,806 B1 | * | 12/2001 | Fox | ................................ 606/80 |
| 6,591,581 B2 | | 7/2003 | Schmieding | |
| 7,879,103 B2 | | 2/2011 | Gertzman et al. | |
| 8,337,780 B2 | | 12/2012 | Gaskins et al. | |
| 8,357,384 B2 | | 1/2013 | Behnam et al. | |
| 8,574,825 B2 | | 11/2013 | Shelby et al. | |

(Continued)

FOREIGN PATENT DOCUMENTS

CN    1861197 A    11/2006

OTHER PUBLICATIONS

Osteosponge, Bacterin, www.bacterin.com.

(Continued)

*Primary Examiner* — Cris L Rodriguez
*Assistant Examiner* — Hao D Mai
(74) *Attorney, Agent, or Firm* — Akerman LLP

(57) ABSTRACT

A method of preparing a bone graft of compressed dehydrated decalcified trabecular bone may include compressing the bone while hydrated from a first form to a second form such that the bone in the second form is compressed relative to the first form. The bone may be dried while compressed. When dry, the bone substantially retains the second form and does not revert to the first form when the compression is removed.

16 Claims, 9 Drawing Sheets

(56) References Cited

U.S. PATENT DOCUMENTS

| | | | |
|---|---|---|---|
| 8,608,801 B2* | 12/2013 | Hung et al. | 623/14.12 |
| 2004/0068234 A1 | 4/2004 | Martin et al. | |
| 2004/0107003 A1* | 6/2004 | Boyer, II | A61B 17/0401 623/23.63 |
| 2004/0169311 A1 | 9/2004 | Bonutti | |
| 2007/0098756 A1* | 5/2007 | Behnam | 424/423 |
| 2007/0231788 A1* | 10/2007 | Behnam et al. | 435/4 |
| 2009/0155378 A1* | 6/2009 | Behnam et al. | 424/549 |
| 2009/0312842 A1 | 12/2009 | Bursac et al. | |
| 2009/0318934 A1 | 12/2009 | Johnson et al. | |
| 2010/0310623 A1* | 12/2010 | Laurencin et al. | 424/423 |
| 2011/0071536 A1 | 3/2011 | Kleiner et al. | |
| 2011/0118850 A1 | 5/2011 | Govil et al. | |
| 2011/0208190 A1* | 8/2011 | Kumbar et al. | 606/70 |
| 2012/0245703 A1* | 9/2012 | Meredith | 623/23.51 |
| 2013/0079889 A1 | 3/2013 | Spillman | |
| 2013/0184835 A1* | 7/2013 | Ferrari et al. | 623/23.61 |
| 2013/0338792 A1* | 12/2013 | Schmieding et al. | 623/23.73 |
| 2014/0005793 A1 | 1/2014 | Koford et al. | |
| 2014/0065239 A9 | 3/2014 | Behnam et al. | |
| 2014/0255506 A1* | 9/2014 | Behnam et al. | 424/549 |

OTHER PUBLICATIONS

International Search Report issued in connection with PCT/US2015/036384.
Written Opinion of the International Searching Authority issued in connection with PCT/US2015/036384.

\* cited by examiner

COMPRESSED DECALCIFIED TRABECULAR BONE GRAFTS AND TOOTH SOCKET REPAIR

FIELD OF THE INVENTION

The present disclosure relates to bone graft preparations. More specifically, the present disclosure relates to bone graft preparations comprising compressed decalcified trabecular bone and use thereof for ridge augmentation and obliteration of tooth socket defects. The present disclosure relates to allograft preparations and methods of supply of allograft preparations specific for a particular tooth or defect regions in a maxilla or mandible.

BACKGROUND

Bone graft treatment for dental applications include mandibular and maxillary ridge augmentations as well as tooth socket obliteration. Empty tooth sockets of various dimensions and shapes are left behind following tooth extraction. If left untreated, the socket fills with blood clot and granulation tissue. In a manner of months, this material is replaced with regenerating bone. Unfortunately, infections during this healing process are common due to the generally contaminated field of the dental defect. Treatment options of such defects include packing the socket cavity with an antibiotic or antiseptic impregnated gauze, synthetic or biological materials including bone allografts or xenografts of particulate bone preparations, blocks of cancellous bone or polymer-based materials, and autologous bone grafts and plasma rich platelets. Bone preparations, for example, are frequently mixed with added carrier materials to provide putties, gels, and pastes intended to improve handling characteristics of the particulate bone. More recently, demineralized cancellous bone preparations characterized by spongy graft materials have been used. The above treatment options take time to heal. Accordingly, if a tooth implant is to be used, the above treatment options must be given time to heal prior to implantation of the tooth implant.

It would be desirable to completely obliterate an empty tooth socket with rapidly healing material that could retain a stem of a tooth implant and that would secure itself by osteointegration. It would similarly be desirable to improve bone graft treatment materials for mandibular and maxillary ridge augmentation.

BRIEF DESCRIPTION OF THE DRAWINGS

The novel features of the described embodiments are set forth with particularity in the appended claims. The described embodiments, however, both as to organization and manner of operation, may be best understood by reference to the following description, taken in conjunction with the accompanying drawings in which:

SUMMARY

Figure 1:
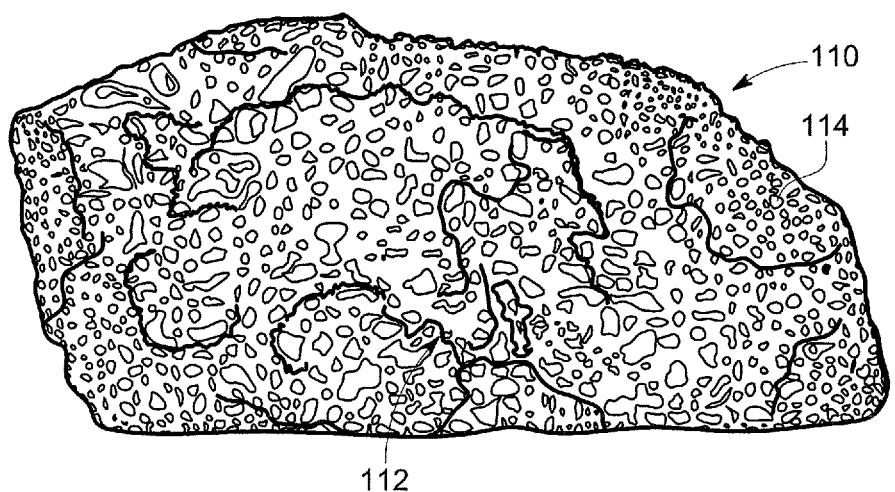
FIG. 1 is a photograph of decalcified cancellous bone demonstrating trabecular architecture.

According to one aspect, the present disclosure is directed to a method of preparing a bone graft that includes compressing and drying bone comprising dehydrated decalcified trabecular bone. The bone may be compressed while hydrated from a first form to a second form such that the bone in the second form is compressed relative to the first form. The bone may be dried while compressed. For example, a compression force may be applied to the bone to compress the bone to the second form and drying may be performed while in the compressed form. When dry, the bone substantially retains the second form and does not revert to the first form when the applied compression is removed or the bone is otherwise released from the compression.

In one aspect, the bone graft comprises an allograft configured for human implantation, while in another aspect the bone graft comprises a xenograft configured for human implantation. In some aspects, the bone comprises 20% to 80% decalcified bone or 50% to 60% decalcified bone. In the first form the bone may define trabecular spaces therein. In the second form, the bone is compressed such that the trabecular spaces are reduced or obliterated. The bone preferably comprises a strip of whole bone sectioned from a larger whole bone and may comprise any desired size or shape, e.g., cross-section, angles, faces, volume, or combination of dimensions, such as cubical, cylindrical, geometric, non-geometric, or irregular in either the first form or the second form. In one aspect, the first form comprises a shape corresponding to that of the second form while in another aspect the first form and the second form comprise different shapes.

In another aspect, compressing the bone includes positioning the bone in a compression device. The compression device may comprise a first wall and a second wall and may be configured to receive the bone therebetween. The first and second wall may define a volume therebetween that is reduced or reduceable with respect to a dimension of the bone in the first form such that the dimension of the bone is compressed to the reduced volume defined between the first wall and the second wall. At least one of the first wall and the second wall may comprise a perforation configured to allow fluid to be released from the bone. The compression device may define a cross-section within the volume between the first wall and the second wall.

In one aspect, drying the bone comprises drying the bone while compressed in the second form. For example, drying the bone may comprise drying the bone while positioned in and compressed by the compression device. In one aspect, drying the bone may comprise hypothermically dehydrating the bone. When dried, the bone in the second form comprises a cross-section complementary to the cross-section defined by the compression device.

In one aspect the method further comprises harvesting whole bone from a donor. The donor may be an animal, which may include a human. The harvested whole bone may be sectioned to obtain sections or strips of whole bone. The harvested whole bone or the sections or strips of whole bone may be preserved, e.g., by dehydration, for subsequent rehydration, e.g., in a decalcifying solution or prior to contacting with decalcifying solution, and use in the method or may be applied fresh.

In some aspects, the method includes decalcifying the bone by contacting the bone with a decalcifying solution. The bone contacted may comprise fresh or dehydrated whole bone that has been sectioned prior to decalcifying the bone to obtain strips of whole bone for the compressing and drying. Contacting may comprise positioning the bone in a bath of the decalcifying solution and performing one or more compression assays during the decalcifying and removing the bone from the bath upon determination the bone has become soft. In some aspects, the decalcifying solution comprises at least one of 1N HCl; citric acid, 5% to 20% w/v; 0.24M disodium or tetrasodium salts of EDTA in a balanced salt solution, saline, or water neutralized to a pH around 6.8 to 7.2 with NaOH; and a mixture of 5M EDTA and 5M citric acid.

In another aspect, a bone graft preparation comprises a dehydrated and decalcified trabecular bone allograft having a compressed form. The compressed form is characterized by reduced or obliterated trabecular spaces relative to an uncompressed form of the bone when hydrated or dehydrated when uncompressed. In one form, the dehydrated trabecular bone allograft having the compressed form is 20% to 80% decalcified. In some forms, the dehydrated trabecular bone allograft having the compressed form is 50% to 60% decalcified.

In yet another aspect, a method of treating maxillary or mandibular defects comprises inserting the bone graft preparation at a maxillary or mandibular defect such that the dehydrated trabecular bone allograft does not revert to the uncompressed form.

In another aspect, a dental implant configured for solid osseous repair or reconstitution of a tooth socket comprises a generally cylindrical shaped body defined by an outer surface and extending along a vertical axis. The body is dimensioned to anatomically conform with at least one dimension of a root of a tooth corresponding to a tooth socket to be repaired or reconstructed. A surface feature extends along the outer surface. The surface feature comprises one or more grooves and is configured to engage tissue at the tooth socket when the implant is implanted therein. The implant is configured for rapid healing and is suitable to support a dental prosthesis upon implantation. The implant may further comprise a biocompatible material comprising one or both of a biological material and a synthetic material. The biocompatible material may comprise at least one of a hydrogel and a metal.

The implant may further comprise compact cancellous bone or cortical bone allograft or xenograft. The implant may be impregnated with an anti-infection agent configured to treat or prevent infection. The implant may comprise perforations defined in the body. The perforations are dimensioned to accommodate stem cells or anti-infective agent. The perforations may be present in a coating on the outer surface of the implant. The outer surface of the implant may comprise a buccal surface portion that is covered with a flexible and pliable collagen membrane. The outer surface may comprise a surface feature. The surface feature may extend from the outer surface. The implant may be provided in a kit comprising a plurality of different dental implants. The implant may be is shaped by a tissue bank to comprise at least one dimension determined from an image of the tooth socket prior to shaping. The body may comprise an aperture extending along the vertical axis configured to receive a post for positioning the prosthesis thereon.

In still another aspect, a method of supplying an implant configured for solid osseous repair or reconstitution comprises receiving measurements, selecting an implant comprising a dimension matched to a size and shape of a tooth root corresponding to a tooth socket, wherein the dimension is determined from measurements comprising a three-dimensional image of a recipient tooth socket to be repaired or reconstituted, and providing the implant to medical personnel for implantation of the implant into the recipient tooth socket.

In one aspect of the method, receiving the measurements comprises receiving a three-dimensional image and a selection of at least one material to be included in the implant. In another aspect, receiving comprises receiving the three-dimensional image and a selection of at least one surface feature to be formed on the implant configured to engage tissue at the tooth socket when the implant is implanted therein.

In one aspect of the method, selecting comprises impregnating the implant with an anti-infection agent configured to treat or prevent infection. In another aspect, selecting comprising generating a specification comprising the dimension determined from the measurements, and the method further comprises shaping the implant according to the specification.

In one aspect of the method, shaping comprises using a computer numerical control (CNC) machine to shape the implant according to the specification. In another aspect, shaping comprises using a CNC machine to shape the implant according to the specification. In another aspect, shaping comprises forming the implant from biocompatible material comprising at least one of a hydrogel and a metal. In another aspect, shaping comprises forming the implant from compact cancellous bone or cortical bone, and wherein the implant comprises an allograft or xenograft.

In still yet another aspect, a system for supplying a dental implant for repair or reconstruction of a particular tooth or defect region in a maxilla or mandible comprises an implant determination module configured to receive measurements or an image from which measurements may be determined of a particular tooth or defect region to be repaired or reconstructed, wherein the implant determination module is configured to generate from the measurements an implant specification from which the implant is to be prepared. The system further comprises an implant shaping module to shape the implant according to the specification. In one embodiment, providing comprises providing the implant in a kit comprising a plurality of different dental implants each comprising a dimension matched to a size and shape of a tooth root corresponding to a respective specific tooth socket.

In one aspect, the implant specification specifies a dimension conforming to a root or portion of a tooth socket corresponding to the particular tooth or defect region to be repaired or reconstructed. The system may further comprise a reception module configured to receive the image or measurements and provide the measurements or image to the implant determination module. In one embodiment, the reception module allows a user to indicate a selection of at least one of: at least one material to include in the implant; at least one measurement to include in the implant specification; at least one surface feature; at least one pre or post shaping conditioning or treatment; at least one support feature configured to support a prosthesis; at least one instrumentation to which the implant is to be compatible; and at least one impregnation treatment. The implant specification may specify the one or more selections. In one embodiment, the system further comprises a treatment module, wherein the treatment module is configured to treat or condition the implant, wherein the treatment comprises at least one of: impregnation with an anti-infection agent; impregnation with stem cells; and application of a coating with a flexible and pliable collagen membrane.

In one aspect, the shaping module is configured to shape the implant from an allograft or xenograft preparation comprising compact cancellous or cortical bone. The system may further comprise a delivery module to deliver the implant to the user. The delivery module may be configured to deliver the implant as part of a kit comprising implantation instruments or additional implants specific additional teeth or sockets. The shaping module may be configured to form surface features on an outer surface of the implant, wherein the surface features comprise one or more of: perforations, threads, grooves, and smooth contours. The shaping module may be configured to form the implant from biocompatible material comprising at least one of a hydrogel and a metal.

In still another aspect, an instrument and method for inserting an implant into a tooth socket comprises a rod extending along a longitudinal axis and comprising a proximal end and a distal end, the rod comprising a curved portion between the proximal end and the distal. A screw portion may be positioned at the distal end of the rod configured to be received within a pre-drilled hole of an implant. A lock may be positioned at the distal end.

DETAILED DESCRIPTION

Bone regeneration may occur if native bone regeneration mechanisms are provided space into which to grow. Thus, an implanted matrix or scaffold into which bone may grow has been used to promote bone regeneration. Typically, regeneration includes absorption or replacement of the implant by the regenerated bone. For example, bone grafts may be used to replace, augment, or repair bone and other structural features in animals including humans. Traditionally, bone grafts may be implanted during a bone grafting procedure in which a bone graft is implanted adjacent to native bone. Bone grafts may comprise various materials harvested or derived from the patient, patient analogues, the same or different species, as well as various natural and synthetic materials and therefore may comprise autografts, allografts, xenografts, synthetics, and combinations thereof.

Osteoinduction is the process that induces osteogenesis or new bone formation by osteoblasts and may include signaling or induction by growth factors. For example, osteoinduction may include native cell recruitment and stimulation of osteoblastic cell differentiation cascades. Osteoconduction generally describes surface phenomenon in which bone growth occurs on a surface. For example, bone grafts preferably comprise implant materials having biocompatible characteristics suitable for osteoconduction. Stable anchorage of bone grafts may be referred to as osseointegration and may include direct contact between native bone and the implanted graft.

According to various embodiments, the disclosed systems, methods, and compositions may include an implant or implant materials such as a bone graft or bone graft materials as described herein configured for implantation into an animal. The implant may be configured to support osteoconduction. In some instances, the implant is configured to provide superior osteoconduction when compared to osteoconduction contributions of conventional implants or bone grafts. For example, the implant may be configured to guide reparative growth of natural bone in a more efficient or directed manner such that bone regeneration results in quicker healing or earlier onset of denser bone regions when compared to conventional implants or bone grafts. In some embodiments, the implant is configured to provide superior osteoinduction when compared to conventional implants or bone grafts. For example, in one embodiment, an implant comprises an allograft of decalcified trabecular bone wherein a greater percentage of growth factors has been retained through the decalcification process to thereby stimulate recruitment and differentiation of native/host cells. In one embodiment, the bone grafts are configured to contribute to bone remodeling.

Techniques for tissue harvesting, e.g., donor graft excision, and preparation vary significantly. And while there have been numerous and generally well-meaning attempts to standardize tissue banking by various voluntary membership organizations, these attempts have, by and large, failed to standardize tissue harvesting and preparation protocols. This is likely due, at least in part, to the voluntary nature of the standards as well as an overall formulation bias toward the tissue banks that promulgate the standards. Among the ways to obtain and prepare bone graft materials is demineralization of structural cancellous bone. However, several deficiencies of current bone grafts, such as bone allografts, remain unaddressed. These deficiencies include porosity attributed to the intertrabecular spaces constituting a major portion of the graft, lack of uniformity, lack of osteoconduction, and lack of mechanical support. Various embodiments of the present disclosure are specifically configured to obviate these and other deficiencies to improve implantation and grafting outcomes.

Mandibular and maxillary bone loss is common, as are problems with dentition, and frequently result in tooth loss or necessitate tooth extraction. According to various embodiments, the herein described implants, grafts, including bone, tooth, organic, synthetic, and other graft materials and compositions thereof, systems and methods of preparation, manufacture, and supply of grafts and implants, as well as related instrumentation, may be configured for use as restorative dental materials and in restorative dental procedures. As explained in more detail below, some embodiments are particularly configured for use in connection with dental procedures. For example, some such embodiments are configured for use in connection with dental procedures comprising dental or tooth implantation, restoration of lost bone, e.g., ridge augmentation, as well as obliteration of tooth sockets following tooth extraction. In some instances, benefits of extraction site grafting according to the present embodiments may include preservation of bone contour for dental implants, denture stability, soft tissue aesthetics, and maintaining periodontal status of adjacent teeth. For example, grafting into extraction sites as described herein may be used to restore gum or jaw following tooth extraction or loss due to congenital defects, periodontal disease, or infections or trauma, for example, or may reduce negative sequela to permit dental implants to be placed in a position that is ideal for function and aesthetics. A graft ridge may also be employed to improve denture stabilization, support, and retention.

In various embodiments, the present embodiments include methods, systems, and apparatuses for preparation, manufacture, and supply of implants and implant material. For example, in one embodiment, a system and method of preparing an implant or implant material comprising a bone allograft specific for a particular tooth in the maxilla and the mandible is described. In some embodiments, for example, an empty tooth socket may be obliterated with a rapidly healing implant material, which may include graft material, to provide, retain, or at least partially support a stem of a tooth implant. In one embodiment, the implant material may be further configured to secure itself by osteointegration and may include biological or synthetic materials such as a gel or metal, e.g., a polymer, hydrogel, or biologically compatible metal. In one embodiment, the implant material comprises compact cancellous bone or cortical bone with one or more surface features, ridges, or perforations. For example, the implant material may comprise a graft of undemineralized or demineralized bone. The implant material may be formed or shaped to a customized dimension using manual, mechanical, or electronic instrumentation based on three-dimensional modeling of an implant site.

In various embodiments, the present disclosure describes systems, methods, and instrumentation for surgical treatment of tooth sockets following tooth extraction as well as apparatuses for preparing implants for such surgical treatments. The implants may comprise grafts and graft materials comprising allografts or xenografts and include compact cancellous or cortical bone. In some embodiments, the bone grafts may be used in a surgical treatment connection with other implant materials, such as a dental implant, tooth implant, or prosthetic.

In one embodiment, an implant includes a bone graft comprising a cancellous bone allograft. The allograft may comprise demineralized cancellous bone that is compressed and dehydrated such that the allograft retains a compact form. In certain embodiments, the implant comprises a bone graft comprising compact cancellous or cortical bone that has not been demineralized. In some embodiments, such bone grafts comprise bone allografts. In one embodiment, the implant includes a body comprising dimensions or features, such as grooves, threads, perforations, or ridges, defined on a surface thereof. Among the suitable applications for certain implants described herein are mandibular and maxillary ridge augmentations and rapid obliteration of tooth socket defects, e.g., in the maxilla or mandible. The present disclosure also includes methods and instrumentation for preparation of implants including bone grafts and methods of treatment using the bone grafts.

Compressed Decalcified Trabecular Bone Grafts

Under normal conditions cancellous bone comprises trabecular bone having trabecular spaces filled with bone marrow, bone marrow precursors, vascular channels, adipose tissue, and other elements. Preparation of trabecular bone for use as an implant or graft may include clearing the bone of the bone marrow, endosteum, and other elements such that the bone is generally composed of trabeculae and spicules that surround the voluminous trabecular spaces. The clearing may be performed mechanically or chemically such that the trabecular spaces remain empty.

Figure 2:
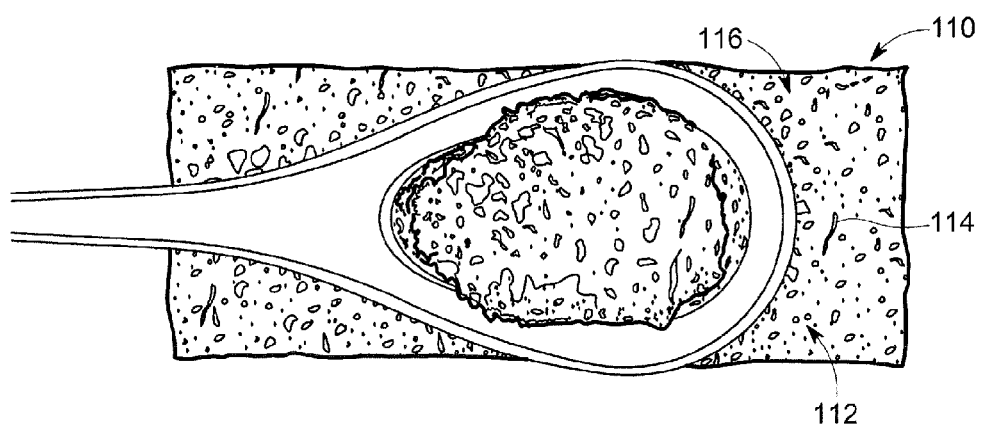
FIG. 2 is a photograph of decalcified cancellous bone compressed by forceps demonstrating the trabecular architecture when compressed.
Figure 3:
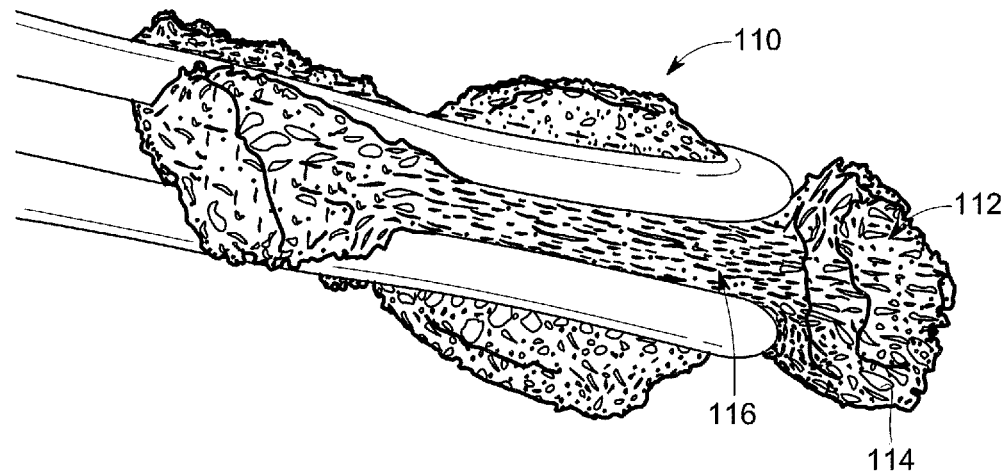
FIG. 3 is a photograph of the decalcified cancellous bone compressed by forceps shown in FIG. 2 further demonstrating the trabecular architecture and characteristic compressibility.

FIG. 1 is a photograph of a decalcified cancellous bone 110 demonstrating the trabecular architecture 112 including the trabecular spaces 114. As depicted in FIGS. 2 and 3, cleared and decalcified trabecular bone 110 is characterized by a compressible structure 116 resembling that of a sponge. For example, the trabecular bone 110 may be compressed from its original or first shape, as shown in FIG. 1, to a second or third shape upon compression, as shown in FIGS. 2 and 3. Upon removal of the compression, the trabecular bone 110 subsequently returns to its first or original precompressed shape. Dehydration of sponge-like grafts comprising trabecular bone 110 that have been cleared or decalcified may also reduce the overall size of the graft whereupon rehydration may result in an increase in size of the graft to return to its pre-dehydrated size. Whether hydrated, dehydrated, or rehydrated, as would occur upon implantation, the trabecular spaces 114 remain. As has now been determined, when a graft preparation comprises such decalcified trabecular bone 110, the empty trabecular spaces 114 may serve to allow vascular ingrowth and reossification of the graft thereby promoting its integration.

In various embodiments, implant materials comprise bone graft materials, preparations, and methods of use comprising compressed dehydrated decalcified, soft trabecular bone.

Figure 4:
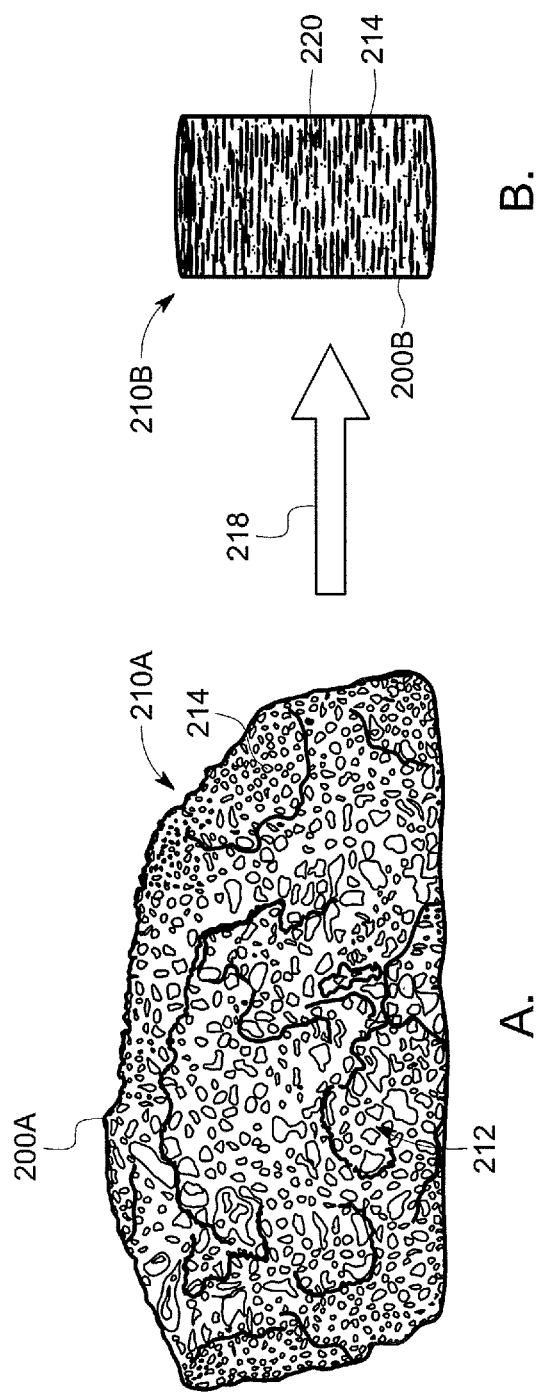
FIG. 4 illustrates a method of preparing a compressed decalcified bone graft preparation according to various embodiments disclosed herein.

FIG. 4 illustrates a graft preparation according to one embodiment. The preparation of graft materials may comprise compressing 218 trabecular bone 200A, which may be similar to the cleared and decalcified trabecular bone 110, to form a bone graft preparation 200B having a compressed structure 220 such that the empty trabecular spaces 214 of the trabecular architecture 212 are either obliterated or reduced in size. The compressed structure 220 of the bone graft preparation 200B is configured to aid in osteogenesis. Additionally, as described below, in various embodiments the bone graft preparation 200B of decalcified trabecular bone may be prepared according to a method configured to aid in osteointegration by providing increased concentration of growth factors such as bone morphogenic proteins (BMPs) and other growth factors per unit of space of the graft compared to conventional sponge-like preparations.

The bone graft preparation 200B comprises decalcified trabecular bone having a compressed structure 220 such that the empty trabecular spaces 214 are obliterated or reduced in size and may include trabecular bone xenografts or allograft preparations. The bone graft preparation 200B is dehydrated upon compression 118 such that the compressed structure 218 is retained when the compression 118 is removed. In various forms, the bone graft preparation 200B may be used in human dental implantation or graft procedures such as those directed to treatment of mandibular or maxillary defects. In some embodiments, the bone graft preparation 200B may be divided into smaller bone graft preparations or bone grafts.

In one embodiment, a method of implanting a bone graft comprising or cut from the bone graft preparation 200B may comprise using customized instrumentation or a set of customized instrumentation having a dimension matched or complementary to the bone graft. For example, in one embodiment, the bone graft preparation 200B is cut to produce a bone graft of suitable dimension for use in a bone graft procedure. Instrumentation may then be selected or provided having a dimension matched to a dimension of the bone graft, which may be the same or a different dimension than the suitable dimension. The instrumentation may be configured to grasp or receive the bone graft at the complementary dimension such that the instrument may guide the insertion and implantation of the bone graft at the grafting site. In one embodiment, precut bone grafts suitable for use in a bone graft procedure may be provided along with the customized instrumentation to implant the bone grafts that have been precut from the bone graft preparation 200B. The precut, compressed trabecular bone graft may include predefined or customized dimensions or diameters configured to complement dimensions or diameters of the customized instrumentation for assisting in insertion of the bone graft. In one embodiment, the customized instrumentation comprises a kit of various dimensioned instruments that may be paired with a plurality of various complementary dimensioned bone grafts. In one embodiment, a bone graft having a desired dimension may be requested and an instrument comprising a complementary dimension configured to receive the bone graft at the complementary dimension may be provided. Following the transplantation procedure, in one embodiment, the instrument may be returned to the provider. Thus a facility or provider may have a customized set of instruments, at least one of which may be provided for use with a paired complementary dimensioned bone graft to assist in the transplantation procedure.

In various embodiments, a method of preparing bone graft materials for use in bone graft preparations includes harvesting or otherwise obtaining a bone, such as a fresh bone or bone specimen, from a bone donor for transplantation into a different or the same organism. According to some applications, the bone may be harvested or excised from a human or a non-human animal. Alternately, the bone may be derived from a human or otherwise be at least partially derived from human origin, prepared under various in-situ or ex-situ environments, including under artificial, laboratory, or human manipulated conditions. It is further contemplated that, in some instances, bone may be bone having non-human origin. Such bone may, for example, have mammalian origin as described above.

Preparation of bone graft materials may further include decalcification of harvested bone. In certain embodiments, the bone is prepared for decalcification fresh, e.g., immediately or soon following harvesting or otherwise closely following obtaining the bone from a donor or biologically maintained environment. In some embodiments, the bone may be prepared or otherwise made to be conveniently available by preserving the bone by, for example, freeze-drying fresh bone. In such instances, the decalcification process may be continued using the freeze-dried bone at a later time. The bone is preferably cleaned and washed when fresh, prior to continuing the decalcification or preservation processes.

In certain embodiments, other suitable preservation techniques may be used. For example, in one embodiment, bone may be preserved by hypothermic dehydration or by chemical dehydration, which is considered herein to be distinct from preservation via freeze-drying techniques. That is, preservation of bone by freeze-drying typically requires freezing the bone prior to drying the bone whereas hypothermic dehydration may avoids freezing altogether. Thus, in one embodiment, fresh bone may be prepared by decalcification at a later date by hypothermic preservation techniques that beneficially prevent damage to the tissue caused by freezing the tissue, e.g., tissue damage induced by ice crystal formation during freezing. Such hypothermic dehydration of bone may employ a technique comprising drying bone tissues in a vacuum at temperatures from 1 to 20 degrees centigrade. The resulting preserved bone may retain characteristics or properties superior to those retained in bone preserved by freeze-drying due to lack of ice crystal induced distortion, collapse phenomenon, or other undesirable characteristics caused by the freezing process of bone preserved by freeze-drying.

Notable confusion exists in regard to demineralized bone matrix (DBM) and demineralized, or more precisely, partially decalcified bone, as the methods of preparation of each is distinct as are their associated biological properties. For example, DBM is prepared from particulate and not structural bone. Preparation of DBM frequently entails freeze-drying, grinding, demineralizing, and then refreeze-drying the bone. Accordingly, DBM is subjected to multiple freeze-drying processes. DBM is also grossly amorphous, soft, and lacks ability to provide structural support. As described herein, bone preparations may comprise decalcified, which includes partially decalcified bone unless described otherwise, that includes trabeculae or trabecular bone that has not been ground and subsequently mixed and reconstituted as is characteristic of DBM. Additionally, in some embodiments, the bone preparations comprise whole, intact, or precut sections of whole bone that may include the ability to provide or promote structural support. Thus, in a preferred embodiment, the bone preparations comprise whole bone. Notably, in one embodiment, ground or bone particulate may be used in addition to whole bone.

According to various embodiments, whole bone or sections of pliable and spongy trabecular bone, e.g., as shown in FIGS. 1-3, may be prepared from donor or harvested trabecular bone. Thus, in one embodiment, donor or harvested bone, may be sectioned prior to or following decalcification by one or more methods. Certain previous methods directed to preparation of DBM specify preparation of particulate bone containing no more than 8% of residual calcium as determined by standard methods such as inductively coupled plasma emission spectroscopy. Decalcification according to the present embodiment may be performed only to render cancellous bone soft and compressible. It may also be used to decalcify cortical bone plates with regular perforations, and then combining these in layers to form a tube which can be shaped into desirable configurations. The residual calcium in the compressible and soft preparations, including those of cortical plates, may also to about 8% of the original level. However, in such instances, the decalcified cancellous bone remains distinguishable from DBM. DBM, as defined by the FDA, is ground and amorphous substance which is shapeless.

In one embodiment, decalcification includes contacting the bone with an acid, such as a strong acid. For example, the bone may be contacted with a HCl solution for a suitable period to decalcify the bone. In one application, the HCl solution is a 1N HCl solution and the suitable period is about 3 hours. It will be appreciated, that varying the strength or concentration of the acidic solution may increase or decrease the suitable period to decalcify the bone to the desired extent. Contacting the bone may include application of the solution to the bone or placing the bone in a bath of the solution and therein submerging all or a portion of the bone. The solution may be agitated to increase contact or coverage. Agitation may also encourage movement of the solution and reduce localized stagnation, bubbles, or variations.

Decalcification in a strong acid bath, such as an 1N HCl bath, may release bone morphogenic proteins (BMPs) from the bone. The release of BMPs may increase the availability of the BMPs to participate in osteogenesis via osteoinduction, however, extended contact with the strong acid bath may further elute BMPs into the bath, which may thereby decrease ostenogenicity due to BMP loss from the preparation. It has been found that many complex factors affect the rate of decalcification and thereby complicate an ability to predict correlations between decalcification solution, degree of decalcification, and type of bone. For example, bones vary by type, location, species, as well as individually. Thus, normalization of decalcification of bone has been shown to be laborious and impractical. As described herein, such undesirable results may be ameliorated by, for example, constant or direct supervision or participation during a decalcification process to prevent excess elution of ostenogenicity promoting factors due to imprecisions in conventional decalcification processes. That is, in one embodiment, instead of immersing bone into an acid bath for a specified period of time, observations or tests may be performed to monitor the process during contact or immersion. For example, a direct relationship with respect to level of demineralization and compression has been ascertained and may be beneficially used to produce superior decalcified bone preparations and bone grafts. In one embodiment, decalcification is conducted under supervision of a technician or operator. The supervision may include exercising direct and constant control of the decalcification process. The supervision may further include intervention by the technician or operator.

As introduced above, the decalcification process comprises performing observations of the bone while contacted with the solution. The observations may be performed during the process by an instrumentation or a technician and may include performing various tests with respect to the bone. In some embodiments, tests performed comprise compressibility assays. For example, the technician may perform a compressibility assay by compressing the bone while the bone is in contact with or submerged in the solution bath. In other embodiments, the technician may remove the bone from the solution bath prior to performing one or more of the compressibility assays. Assays may also be performed by applying a compression force to the bone using an implement, e.g., a surface positioned on a rod, tongs, or by placing a weight on the bone. In one embodiment, the implement may comprise, for example, a glass, ceramic, or other material able to withstand the acidic environment of the solution. In another embodiment, compressibility assays comprise removing the bone from contact with the solution prior to compressing the bone and returning the bone to contact the solution upon determination that the bone has not achieved a pre-determined compressibility. In a preferred embodiment, the bone is removed from contact with the solution as soon as or as close as possible to the time it is determined that the pre-determined desired compressibility or pliability is present.

In various embodiments, observations of the bone may be taken during the decalcification process. Observations may be continuous or taken at scheduled or periodic intervals. Depending on the protocol, the scheduled intervals may be periodic, variable, consistent, or otherwise different. For example, the time between scheduled intervals may decrease during the duration of the process. Observations may similarly be based on protocols wherein the results from tests, such as compressibility assays, or other observations may be used to determine or adjust timing of subsequent observations or otherwise may identify additional tests that are to be performed.

It is to be appreciated that the technician need not be a human in all embodiments. Indeed, in one embodiment, the technician comprises instrumentation configured to measure, quantify, or determine compressibility of bone during the decalcification process. Such instrumentation may be automated or under the control of the operator. The instrumentation may be configured or programmed to perform compressibility assays in addition to or instead of compressibility assays that may be performed by the technician or operator, whether manually or with assistance from an electronic device configured to assist the technician in determining compressibility. In one embodiment, the automated instrument includes or is coupled to a special purpose computer configured to run a program, e.g., an algorithm embodied in software stored in a data storage medium, to perform compressibility assays and remove the bone upon determination of a pre-determined compressibility. The program may be embodied in instructions, such as electronic instructions, written or encoded on a computer readable medium or stored on an electronic storage device. The program may be software executable by the computer via a control module or processor. Tests may also include other methods of determining decalcification such as eluted mineral content in the solution bath, for example. In one embodiment, an electronic device or computer programmed to perform one or more observations or tests may be used in conjunction with instrumentation to determine desired level or degree of decalcification.

According to the various embodiments, other or additional decalcification methods may be used. For example, in one embodiment, trabecular bone may be decalcified by contacting the bone with weakly acidic or neutral solutions. Indeed, in some embodiments, such a neutral solution comprising ethylenediaminetetraacetic acid (EDTA) may be contacted with bone in a milder decalcification process. EDTA as a histological demineralization agent provides for histological demonstration of enzymes such as phosphatases as well as other enzymes, e.g., hydrolytic and oxidative enzymes. Under appropriate conditions, enzymatic activity of such enzymes is noted to be unaffected up to 30 days. EDTA may also have beneficial application as an antiseptic agent and enzyme purifier. Notably, compared to strongly acidic solutions, e.g., 1N HCl, the EDTA acts slowly. For example, decalcification using EDTA may require multiple days, such as between 72 to 120 hours. Similar to EDTA, citric acid may be used as a mild or slow acting decalcification agent. Accordingly, in some embodiments, bone may be contacted with a solution comprising citric acid for decalcification. The citric acid may be, for example, in the form of sodium salts.

In one embodiment, a solution for decalcification of trabecular bone with substantially no loss of desirable enzymes, enzymatic activity, or BMP comprises EDTA and citric acid. While the precise amounts of EDTA and citric acid may be modified to optimize use of the solution with respect to particular types or sizes of bone, conditions, speed of decalcification, and other considerations, in one embodiment, the decalcification solution comprises EDTA (0.5M) and citric acid (5M) in the form of sodium salts. In various embodiments, the above solution preferably comprises a neutral pH. In one embodiment, trabecular bone is decalcified by exposure to a 5% to 20% citric acid solution. In one embodiment, trabecular bone is decalcified by exposure to a 5M EDTA, 5M citric acid solution. The solution may be preferably neutralized to a pH around 6.8 to 7.2, e.g., with NaOH. In another embodiment, trabecular bone is decalcified by exposure to a solution comprising about 10% or 0.24M EDTA in a phosphate buffered saline, or other balanced salt solution, saline, or water. The solutions may be preferably neutralized to a pH around 6.8 to 7.2, e.g., with NaOH.

In various embodiments, the demineralization process comprises preparation of trabecular bone allografts by contacting bone with a decalcification solution as described herein. The allografts preferably comprise beneficial characteristics such as softness, pliability, and compressibility. As described above, the decalcification solution may comprise an EDTA-citric acid solution or, if rapid decalcification is needed, a HCl solution, or a combination thereof.

In various embodiments, a method of preparing bone graft preparations may include decalcifying bone according to any of the methods described above. In some instances, as illustrated in FIG. 4, the method further includes compressing 218 the decalcified bone 200A, including partially decalcified bone, having a first form 210A to prepare a bone graft preparation 200B comprising compressed decalcified bone having a second form 210B compressed with respect to the first form 210A. The bone graft preparation 200B may therefore comprise the decalcified bone 200A bone that has been compressed 218 such that the preparation 200B comprises concentrated BMPs. Compression 218 may include compacting the decalcified bone 200A and thereby decreasing a dimension and volume or obliterating the trabecular spaces therein. Compression 218 may therefore increase the BMP density or concentration thus aiding in osteogenesis and allograft integration by rendering the decalcified bone graft preparation 200B osteoinductive.

Figure 5:
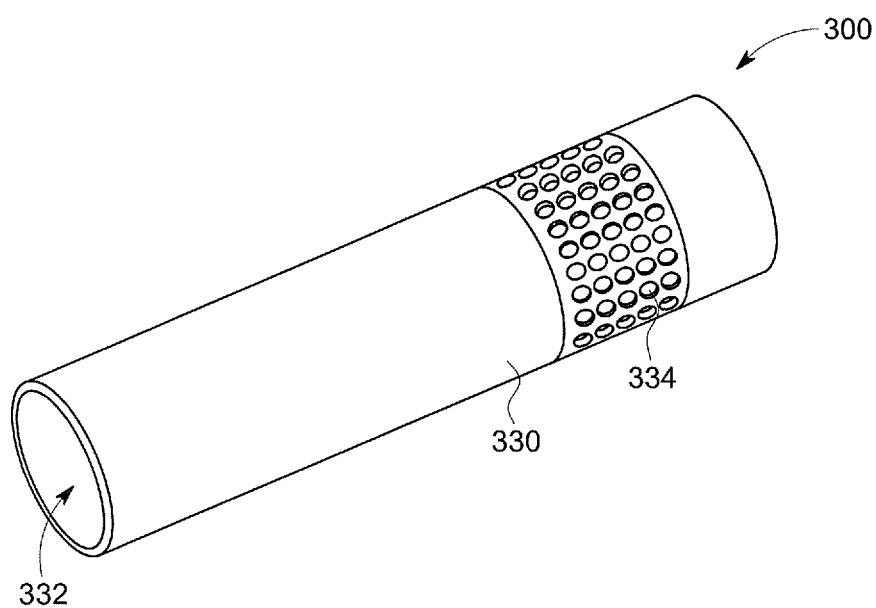
FIG. 5 illustrates an apparatus for preparing a compressed decalcified bone graft preparation according to various embodiments disclosed herein.

After decalcification, the whole or sectioned trabecular bone may be cut into strips to be compressed 218. Compression 218 may be performed by compressing the bone while allowing fluid to escape. FIG. 5 illustrates one embodiment of an apparatus 300 configured to compress the decalcified bone 200A. The apparatus 300 comprises one or more walls 330 that define a bore 332 dimensioned to receive the decalcified bone 200A. Thus, in one embodiment, a method of compressing decalcified bone 200A comprises inserting the decalcified bone 200A in the bore 332 of the apparatus 300. The apparatus 300 comprises walls 330 configured to constrict or oppose decompression of the decalcified bone 200A to the first form 210A when positioned therebetween. The dimensions of the bore 332 defined by the walls 330 are configured to further define a desired compressed shape 210B of the compressed decalcified bone preparation 200B. In the illustrated embodiment, the walls 330 are generally arcuate and define a cylindrical bore 332 configured to compress decalcified bone 200A to produce the cylindrically shaped 210B compressed decalcified bone preparation 200B. While the desired size and dimensions of the decalcified bone preparations 200B will generally be chosen in consideration of the application, as described below, the illustrated apparatus may be configured to compress decalcified bone 200A into second forms comprising cylinder shapes 210B between 5 mm and 30 mm. It is to be appreciated that the apparatus 300 may comprise any number of walls 320 configured to compress decalcified bone 200A into any desired size and geometrical or non-geometrical shape to produce a compressed decalcified bone preparation 200B having the desired size and shape of a second form 210B.

The decalcified bone 200A is generally dried in the compressed second form 210B to produce the compressed decalcified bone 200B such that the compressed decalcified bone 200B maintains the compressed structure 220 and desired second form 210B upon removal of the compression 218, e.g., upon removal from the apparatus 300. As illustrated in FIG. 5, the walls 330 of the apparatus 300 further comprise one or more perforations 334. The perforations 334 may be provided in a number and arrangement configured to allow fluid to escape adjacent to or around the decalcified bone 200A when resident in the bore 332. The number and arrangement of perforations 334 may also be configured to allow an increased surface area of the decalcified bone 200A to be exposed for dehydration while compressed 218. In one embodiment, decalcified trabecular bone 200A having a first form 210A is compressed 218 using the compression apparatus 300 while in a hydrated state, as shown in FIG. 4. The compression 218 compresses the decalcified bone 200A to a second form 210B that is compressed with respect to the first form. To avoid decompression from the second form 210B to the first form 210A upon removal from the apparatus 300, similar to a sponge, the decalcified bone 200A is dried or dehydrated while in the second form 210B. Accordingly, the compressed decalcified bone preparation 200B comprises dehydrated decalcified bone configured to retain the second form 210B having a compressed structure 220 such that the empty trabecular spaces 214 of the trabecular architecture 212 are either obliterated or reduced in size.

In some embodiments, drying of the decalcified bone 200A is performed in the apparatus 300 or another compression apparatus configured to receive the compressed decalcified bone and comprising a desired dimension to impart upon the compressed decalcified bone preparation 200B. For example, upon compression 218 from the first form 210A to the second form 210B, drying or dehydrating may be employed to retain the second form 210B. The second form 210B is reduced in size or dimension relative to the first form 210A in a hydrated state or the decalcified bone 200A dehydrated while uncompressed. For example, the bore 332 may comprise a cross-section and volume defined between the one or more walls 330 configured to compress 218 the decalcified bone 200A to a volume and cross-section corresponding to the bore 332 such that when dehydrated the second form 210B is retained to produce the compressed decalcified bone preparation 200B. The dehydration process may be assisted by increased gas flow or thermal variations. For example, the perforations 334 in the walls 330 of the apparatus 300 may be configured to allow hydrating fluids to escape the decalcified bone during compression and drying. The perforations 334 in the walls 330 may be further configured to increase available or exposed surface area of the decalcified bone 200A to gas or circulation of gas. In one embodiment, hypothermic dehydration may be employed to dry the decalcified bone 200A while compressed in the second form 210B and resident in the bore 332 of the apparatus such that the compressed decalcified bone preparation 200B retains the second form 210B in a dehydrated state.

Figure 6:
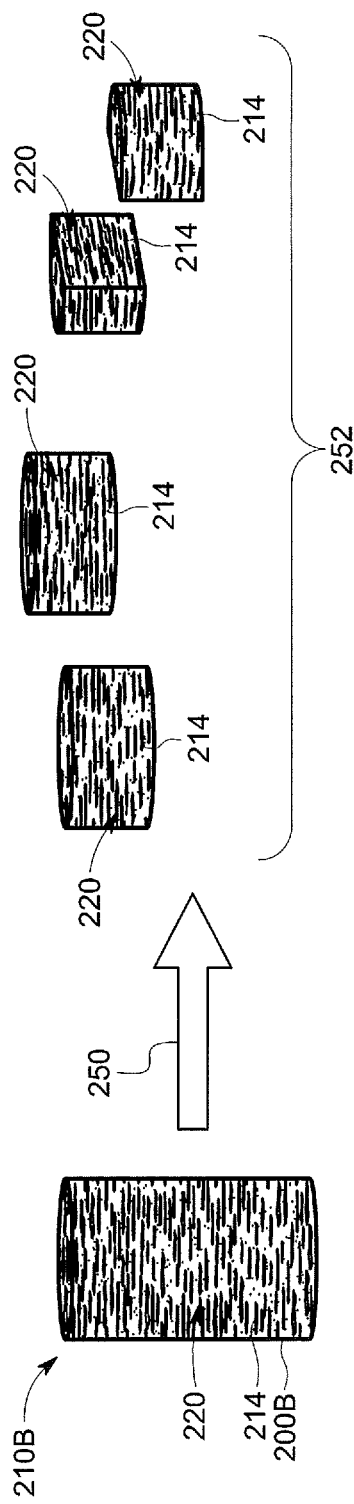
FIG. 6 illustrates a method of cutting a compressed decalcified bone graft preparation to form compressed decalcified bone grafts according to various embodiments disclosed herein.

In various embodiments, referring to FIG. 6, the compressed decalcified bone preparations 200B may be cut 250 into grafts 252 dimensioned for delivery into a recipient. Thus, grafts 252 may be conveniently cut 250 to comprise various customized desired dimensions. As described above, the compressed decalcified bone preparations 200B may be compressed into a second form 210B that may comprise a desired dimension. Thus cutting 250 the preparations 200B may further refine the desired dimension or may obtain a different or additional desired dimension or size. In one embodiment, a compressed decalcified bone preparation 200B may be cut to produce grafts 252 having desired dimensions complementary to a delivery device configured to receive or retain the graft 252 for delivery of the graft 252 at the grafting site. For example, a preparation 200B comprising compressed decalcified trabecular bone may be further but into grafts 252 comprising a desired size and shape comprising a cubical, cylindrical, spherical, arcuate, or other regular or irregular geometric shape. In one embodiment, the complementary dimension with respect to the delivery device may be matched with a desired dimension defined by the grafting site of the recipient.

Methods and Instrumentation for Using Compressed Decalcified Bone Grafts

In various embodiments, a graft 252 of compressed decalcified bone comprises a dimension corresponding to a dimension defined by an internal bore of a delivery tube configured to receive and deliver the graft 252. For example, the cross-section of the graft 252 may be complementary to at cylindrical, arcuate, round, geometric, non-geometric, or irregular cross-section, etc. of the delivery tube. In one embodiment, the graft 252 comprises a cylindrically shaped allograft comprising an arcuate cross-section that is dimensioned for insertion into the delivery tube defining a complementary cylindrical or arcuate cross-section. The delivery tube may include or be configured for coupling to a handle. The handle may include a coupling configured to couple to the delivery tube. A tamp may be operatively associated with the delivery tube and be configured to expel or selectively expel the graft 252 into a grafting site comprising a recipient defect. The tamp or separate instrument may be further used to finely position the graft at the defect. In some embodiments, the separate instrument comprises a tap having a handle configured to tap the graft 252 at the recipient defect to finely position or seat the graft 252. The tap may be received through and be therein guidable by the delivery tube or coupling member or may be configured to operate separately of the delivery tube or coupling member.

Figure 7:
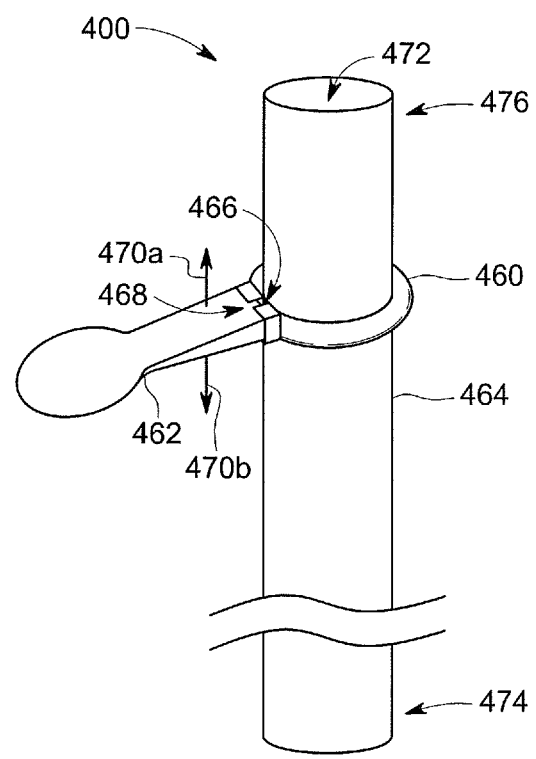
FIG. 7 illustrates a delivery device according to various embodiments disclosed herein.

One embodiment of a delivery device is shown in FIG. 7. The delivery device 400 comprises a ring coupling 460 attached to a handle 462 and configured to receive a delivery tube 464. In certain embodiments, the coupling 460 is configured to receive the delivery tube 464 such that the delivery tube may at least partially translate with respect to the coupling 460 while coupled thereto. The coupling 460 may include one or more features configured to provide a desired friction with respect to the delivery tube 464. For example, the coupling 260 may comprise a smooth surface, bumps, or ridges disposed along an inner ring surface 466 configured to contact the delivery tube 464 to decrease friction. The inner ring surface 466 may comprise a rough surface or comprise a material configured to increase friction in one or more directions. In one embodiment the coupling 460 may limit the extent of translation in one or more directions. For example, stops may be provided or bristles may be positioned within the coupling 460 to increase friction in a first direction and decrease friction in a second direction. In some embodiments, the coupling 460 may be configured to selectively limit one or both of rotation or translation of the delivery tube 464. For example, the coupling 460 may include a clamping feature configured to selectively compress or retain the delivery tube 460. In one embodiment, the coupling 460 comprises one or more grooves configured to mate or be received by one or more complementary grooves positioned on the delivery tube 464.

In general, a user may use the handle 462 for manipulation of the coupling 460 or delivery tube 464. For example, the handle 462 may comprise a dimension configured to be grasped by the user or a stabilization device to maintain a desired angle of delivery. The handle 462 may be coupled to the coupling 460 via a fixed or multi directional coupling 468 to allow the user to position the handle 462, generally in direction indicated by arrows 470a, 470b, to adjust an angle in which the delivery tube 464 is positioned with respect to the handle 462 and coupler 460. The delivery tube 464 may comprise any desirable dimension. Preferably, the delivery tube 464 defines a channel 472 dimensioned to receive the graft 252 therein such that the graft may be movable therethrough by a tamp (not shown). In some embodiments, a dimension of the delivery tube 464 is matched to a dimension of the graft 252 such that the dimensions are complementary for better fitment for delivery. For example, the delivery tube 464 may define an arcuate cross-section configured to receive a cylindrical graft 252, such as a compressed cylindrical allograft of decalcified trabecular bone. The delivery tube 464 may be formed of rigid or flexible material. For instance, the delivery tube 464 may comprise a lumen or cannula adapted for an endoscopic procedure. While the delivery tube 464 may be opaque, in one embodiment, a length of the delivery tube 464 is clear or translucent to allow the user to visualize the position and delivery of the graft 252. In one embodiment, the delivery tube 464 provides an alignment guide or stabilizer during delivery to the grafting site as well as during implantation. In various embodiments, the tamp or a separate tap may be used to further assist in implantation. For example, the tamp may comprise a handle and be translatable within the delivery tube 464 to deliver the graft 252 to the grafting site. The tamp may be further extended, in some instances, beyond a distal end 474 of the delivery tube 464 to position the graft 252 at a desired location, e.g., at a defect. In one embodiment, the tamp may be withdrawn from the delivery tube 464 and a tap comprising a handle or other instrument may be inserted at the proximal end 476 of the delivery tube 464 and therein extended to the distal end 474 to further position, seat, or implant the graft 252, e.g., tap the graft 252 into a defect such as a recipient tooth socket.

According to one method, the distal end 474 of the delivery tube 464 may be positioned proximate to a grafting site, e.g., a tissue defect, tooth socket to be obliterated, etc. The graft 252 may be received at the proximal end 476 of the delivery tube 464 before or after positioning the distal end 474 of the delivery tube 464. In embodiments wherein the delivery device 400 is configured to include a coupling 460 to operatively associate the delivery tube 464, the delivery tube 464 may be coupled with the coupling 460 for positioning the distal end 474 of the delivery tube 464 proximate to the grafting site or to maintain or stabilize a position relative to the grafting site. For example, as depicted in FIG. 7, when the delivery tube is received within the ring coupling 460, the handle 462 may be used to guide or further stabilize the positioning of the delivery tube with respect to the grafting site. To deliver the graft 252, a user may grasp a handle attached to the tamp and extend the tamp from the proximal end 476 to the distal end 474 of the delivery tube 464. Once the graft 252 is delivered to the grafting site, the tamp or additional instrument may be used to position the graft 252 for implantation into the grafting site. For example, a user may insert a tap through the delivery tube 464 or position the tap without the delivery tube 464 using a handle attached to the tap and tap the graft 252 to seat the graft 252 at the grafting site, e.g., recipient defect.

In one embodiment, the recipient defect comprises a defect in an oral cavity such as a tooth socket ready for obliteration. The delivery tube 464 may be inserted into the recipient's oral cavity and the distal end 472 may be positioned proximate the grafting site comprising a tooth socket defect. The delivery tube 464 may be further coupled with the ring coupling 460 to provide increased stability of the delivery tube 460 during the procedure. The user may then distally extend the tamp to deliver the graft 252 from the distal end 472 of the delivery tube 464 to the tooth socket. The tamp or a tap may be further employed to finely position or seat the graft 252 in the socket as described above.

According to various embodiments, a graft remover may be provided. The graft remover may be configured to remove a graft 252 from a recipient's tooth socket during or after insertion of the graft 252. For example, it may be desirable to remove or reposition a graft 252 that has been seated too deeply or for various other reasons. Thus, the above grafts 252, apparatuses, methods may include tooth socket obliteration including removal of a graft 252 when needed.

Dental Implants for Osseous Repair or Reconstruction

In various embodiments, tooth socket repair comprises preparation, supply, or implantation of an osseous dental implant. According to certain embodiments, an implant is configured for rapid healing and is suitable to support a dental prosthesis upon implantation. According to various embodiments, the implants comprise general conical shapes and may be referred to herein as a conical plug configured for use as osseous implants. The implants or conical plugs, in some embodiments, may further comprise grafts configured to be inserted in a tooth socket to achieve rapid healing of the socket or accommodate a tooth or other implant. The implants may comprise an osseous bone graft implant as described herein and may comprise compact cancellous or cortical bone, which may or may not be demineralized. The implants may comprise a cylindrical conical preformed plug of cancellous or cortical bone implant comprising a human allograft or an animal tissue xenograft.

Figure 8:
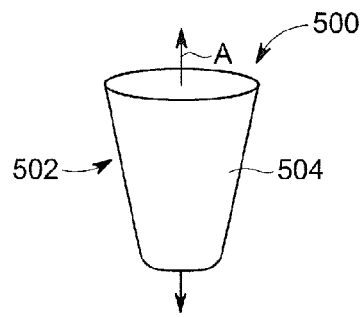
FIG. 8 illustrates an elevated view of an osseous implant according to various embodiments disclosed herein.
Figure 9:
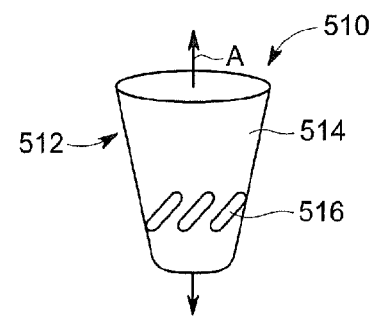
FIG. 9 illustrates an elevated view of an osseous implant according to various embodiments disclosed herein.
Figure 10:
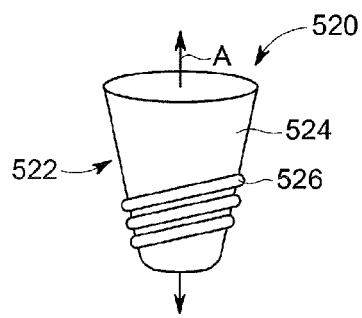
FIG. 10 illustrates an elevated view of an osseous implant according to various embodiments disclosed herein.
Figure 11:
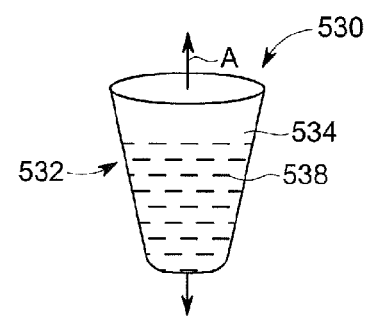
FIG. 11 illustrates an elevated view of an osseous implant according to various embodiments disclosed herein.
Figure 12:
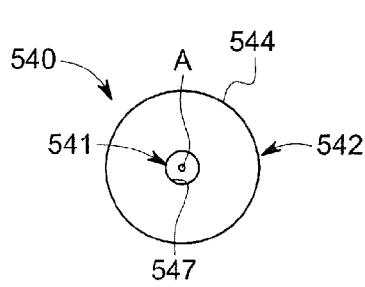
FIG. 12 illustrates a top view of an osseous implant according to various embodiments disclosed herein.
Figure 13:
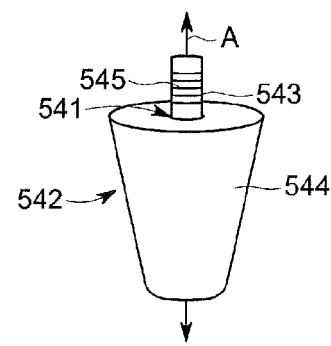
FIG. 13 illustrates the osseous implant illustrated in FIG. 12 according to various embodiments disclosed herein.

In various embodiments, referring to FIG. 8, an osseous dental implant 500 configured for solid osseous repair or reconstitution of the tooth socket comprises a generally cylindrical shaped body 502 defined by an outer surface 504 and extending along a vertical axis A. The body 506 is dimensioned to anatomically conform with at least one dimension of a root of a tooth corresponding to a tooth socket to be repaired or reconstructed. FIGS. 9-13 illustrate various embodiments of implants 500 showing represented examples of a variety of features categories. It is to be understood that implants may include any or all the categories of features identified as well as the variety of variations applicable to each category of feature. As shown in FIG. 9, in various embodiments, an implant 510 comprises a generally cylindrical body 512 and one or more surface features 516 may extend along an outer surface 514. The surface features 516 comprise one or more grooves and are configured to engage tissue at the tooth socket when the implant 510 is implanted therein. FIG. 10 illustrates another embodiment of an implant 510 comprising a generally cylindrical body 522 and one or more surface features 526 extending along an outer surface 524 of the implant 520. The surface features 526 comprise angled grooves having a helical pattern configured to engage tissue at the tooth socket when the implant 520 is implanted therein. In one embodiment, the implant 500, 520, 520 may be impregnated with an anti-infection agent such as an anti-septic, anti-microbial, etc. Impregnation may include impregnating perforations formed in or at the outer surface 502, 512, 522 of the implant. For example, FIG. 11 illustrates an embodiment of an implant 530 comprising perforations 538 formed in the outer surface 534 of the body 532. In other embodiments, perforations 538 may be completely or partially internalized and comprise impregnation cells. In one embodiment, the implant 500, 510, 520, 530 comprises perforations 538 configured to contain or be impregnated with stem cells. In certain embodiments, the implant 500, 510, 520, 530 comprises an aperture extending along the vertical axis A configured to receive a post for positioning the prosthesis thereon. FIG. 12 illustrates a top view of an implant 540 that may be similar to implants 500, 510, 520, 530 comprising an aperture 541 formed in the outer surface 546 of the body 542 along the vertical axis A. As shown in FIG. 13, the aperture 541 is configured to receive a post 543. The post 543 includes threads 545 for attachment of a prosthesis. In one embodiment, the post 543 may be configured to be received or coupled to another implant, such as a tooth implant, and may comprise grooves, threads, or a progressively increasing diameter from the top of the post toward a top surface of the implant. It will be appreciated that other forms of attachment may be provided including clips, brackets, adhesives, compression fittings, etc. In various embodiments, the aperture 541 may be tapped or internally threaded 547 to assist in receiving and retaining the post 543. Again, other forms of retaining the post may be used, such as ridges, grooves, compression, self-tapping, adhesives, etc.

The implants may comprise various materials including, for example, natural bone, synthetic materials, metals, ceramics, polymers, and blends thereof. In one embodiment, an implant comprises a cancellous or cortical bone allograft or xenograft configured for obliterating the tooth socket. In some embodiments, an implant comprises a biocompatible material comprising one or both of a biological material and a synthetic material. The biocompatible material may comprise, for example, a hydrogel or a metal. In various embodiments, an implant may comprise perforations, which may be similar to perforations 438, present in a coating on at its outer surface. The outer surface may comprise a buccal surface portion that is covered with a flexible and pliable collagen membrane.

In certain embodiments, the implants comprise a cancellous or cortical bone allograft or xenograft configured to support a dental prosthesis immediately or approximately immediately following implantation of the implant. For example, the implant may be configured to support and retain a stem of a tooth implant during the same operative session or on the same day as the implantation procedure. An operative session for implantation of the implant, for example, may comprise a primary graft implantation procedure wherein the implant is implanted in a recipient tooth socket and one or more secondary procedures. In some embodiments, the secondary procedure comprises extraction of a tooth from the tooth socket prior to implantation or the implant or fixation of a prosthesis to the implanted implant. In one embodiment, the secondary procedure comprises both extraction of a tooth from the tooth socket prior to implantation or the implant and fixation of a prosthesis to the implanted implant. Accordingly, the implant may comprise a graft that is implantable in a tooth socket and configured to provide a stable association with the obliterated tooth socket and a prosthesis. Beneficially, the implant may be configured to provide the stable associations immediately or during the implantation procedure in which the implant is implanted in the tooth socket.

Systems and Methods for Supply of Anatomically Specific Implants

In one embodiment, a system and method of preparing and supplying the implants comprises shaping the implants by a tissue bank to comprise at least one dimension specific to a tooth socket or tooth associated with the tooth socket to be repaired. The at least one dimension may be determined from an image of the tooth socket prior to shaping. In various embodiments, an implant is provided in a kit comprising a plurality of different dental implants. According to one embodiment, a recipient tooth socket may be measured, e.g., imaged for measurement, prior to an implantation procedure within an office setting. Measurements preferably comprise at least one anatomical measurement related to the tooth socket. The measurements or image for measurement may be sent to an osseous implant supplier for selection of an implant having at least one anatomically matched dimension. The supplier may take the measurements or image to prepare or form an implant comprising an anatomical dimension specified by the measurements or image to anatomically match the dimension of the implant to the tooth socket. The implant may also be selected from a selection of pre-formed implants comprising an anatomically matched dimension. In one embodiment, the selected pre-formed implant may be further modified in at least one anatomical dimension specified by the image or measurement sent to the supplier to form a customized or specifically preformed implant, e.g., using a CNS machine, molds, or handmade. In one embodiment, a supplier forms an implant in accordance with at least one of the measured anatomical aspects of the tooth socket to form an implant specific for the tooth socket. According to some embodiments, the user may provide certain design considerations to which the implant is to conform. For example, the user may request material compositions, surface features, or coatings. The implant supplier may have a website, program, or form into which a user may select from various compositions, surface features, or coatings. Thus, in various embodiments, the selected implant may be selected entirely by the user or the supplier according to the images or measurements provided by an imaging party. In other embodiments, the selected implant may include various selected aspects by a user in conjunction with standards selected by the implant supplier. Accordingly, the selected implant having an anatomically matched dimension may be provided, e.g., sent or delivered, for insertion by the user, such as medical personnel. The user may thereafter insert the implant into the specific recipient tooth socket during an implantation procedure to obliterate the tooth socket.

Figure 14:
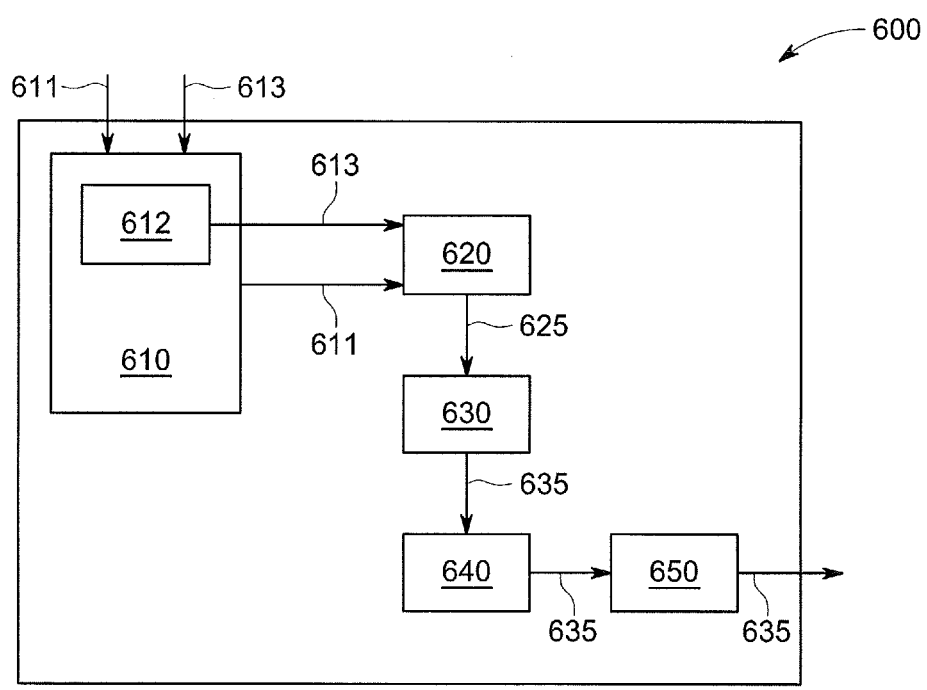
FIG. 14 is a schematic representation of a system for supplying a dental implant for solid osseous repair or reconstitution according to various embodiments disclosed herein.

FIG. 14 is a schematic of a system 600 for supplying a dental implant for solid osseous repair or reconstitution. As described herein, the system 600 may be configured for supplying a dental implant 635 for repair or reconstruction of a particular tooth or defect region comprising a maxilla or mandible. The system 600 includes a reception module 610, implantation determination module 620, shaping module 630, treatment and conditioning module 640, or delivery module 650, as described more fully below. According to various embodiments, system 600 may comprise a computer implemented system comprising instructions embodied in software stored on a computer readable medium configured to be executed by a processor. The system 600 may be configured to run on a user device, such as a computer, or may be configured to be accessed through one or more networks, e.g., a distributed network, and run on a server associated with the implant supplier. Thus, a party may image a recipient tooth socket and then run a program to obtain one or more anatomical measurements 611 related to the tooth socket or associated tooth or root. The measurements 611 are preferably determined by a computer program, which may be associated with the implant determination program associated with the implant determination module 620. Thus, a portion of the system 600 may be provided on multiple programs at multiple locations. In one embodiment, images are transmitted to the implant supplier server comprising various system 600 modules preparation of implants 635. An implant specification 625 may be generated on the supplier server or received by the reception module 610, for example when the implant determination module 620 in whole or in part is operated from a user device as a separate program configured to operatively communicate or provide implant specification 625 data points from which the implant 635 is to conform.

The system 600 for supply of dental implants 635 may include receiving, e.g., via a reception module 610, measurements 611, such as an image, or in some embodiments a selection 613 of implant 635 features, characteristics, or materials. Receiving measurements 611 may include receiving numerical measurements, references to measurements or images, images, or three-dimensional imaging, for example. The measurements 611 may be received from an imaging party, such as a patient, medical professional, technician, third-party imager, clearing house, etc. The image may, for example, be transmitted electronically to dedicated servers, by mail, or by hand. When the reception module 610 comprises a computer implantation, the images may be received by or input into the reception module 610.

In one embodiment, the system 600 further includes receiving a selection 613 in addition to the measurements 611. Thus, in various embodiments, the reception module 610 may comprise a selection module 612 into which one or more selections 613 may be selected or identified. According to various embodiments, the reception module 610 comprises a computer program, website, or other resource into which a user may identify and the system 600 may receive the selection 613. The selection may include a material at least one material to be included in the implant 635, at least one surface feature to be formed on the implant 635, at least one material to impregnate the implant 635, e.g., an anti-infection agent, stem cells, BMPs, signaling molecules, or bioactive agents. For example, the user may specify particular dimensions for the implant 635. The reception module 610 may include selection and receipt of at least one surface feature to be formed on the implant 635, as described herein. The reception module 610 may include selection and receipt of at least one pre- or post-shaping conditioning or treatment or selection and receipt of at least one support feature configured to support a prosthesis. For example, the selection may include a dimension to be formed in the implant 635 such as an aperture or attachment point. Similarly, the reception module 610 may include selection and receipt of at least one instrumentation to which the implant 635 is to be compatible.

In various embodiments, the reception module 610 is configured to provide the measurements 611 or selections 613 to the implant determination module 620. The implant determination module 620 may be configured to receive measurements 611—or an image from which measurements 611 may be determined—of a particular tooth or defect region to be repaired or reconstructed. The implant determination module 620 may also be configured to generate from the measurements 611 an implant specification 625 from which the implant 635 is to be prepared. The implant specification 625 may, for example, specify dimension conforming to a root or portion of a tooth socket corresponding to the particular tooth or defect region to be repaired or reconstructed, a dimension to be formed in the implant 635, surface features, instrumentation, impregnation, construction materials, a coating, a pre- or post-treatment or conditioning, or a type of aperture or attachment point to include. The implant determination module 620 is configured to generate an implant specification 625 from which the shaping module 630 and associated instrumentation may use to select, form, or shape the implant 635. Accordingly, measurements 611 of a recipient tooth socket may be received, e.g., in the form of numerical measurements, references, images, by the reception module 610. The measurements 611 may be a three-dimensional image or a plurality of images taken from different positions relative to the tooth socket. The images may be transmitted to the implant supplier by a user via the reception module 610 for selection or preparation according to the implant specification 625. As stated above, in some instances, a user may operate an implant determination program configured to generate an implant specification 625 that may be sent to the reception module 610. In such a case, the implant specification 625 may be reviewed by the determination module 620 or may be provided to the shaping module 630 for shaping according to the implant specification 625. In various embodiments, the implant determination module 620 is configured to generate the implant specification 625 including determination or identification of at least one anatomical dimension specific to a tooth or the tooth socket to be repaired such that the implant 635 is anatomically specific to the recipient tooth socket in the at least one anatomical dimension. In one embodiment, the implant determination module 620 comprises a computer program configured to determine an implant material based on a plurality of data points. For example, the implant determination module 620 may comprise an algorithm configured to select suitable materials, shapes, or dimensions based on data points descriptive of the tooth socket, e.g., measurements 611, as well as other information provided to the reception module 610, such as specific application, medical history, or biographical information relating to the recipient. In some instances, the implant determination module 620 is configured to consider a selection of material received by the reception module 610 as a data point, which in one embodiment, may operate as an override with respect to all or a portion of the algorithm. Implant materials identified in the implant specification 625 may include, e.g., biocompatible materials including polymers, synthetic bone graft materials, metals, biologically active molecules such as growth factors or signaling molecules, pharmaceuticals, anti-infective agents, biological materials such as stem cells, among other suitable materials.

In one embodiment, the system 600 includes instrumentation for preparing the implants 635. Instrumentation may be operated manually or electronically, for example, according to pre-programed instructions. The instrumentation may include rendering devices configured to form implants 635 according to the measurements 611 or images of each tooth or tooth socket. For example, a three-dimensional image of a tooth or socket may be transmitted to an implant determination module 620. The implant determination module 620 may use the image to provide an implant specification 625 to a shaping module 630 configured to shape the implant 635 according to the specification 625. Thus, in various embodiments, the system 600 may also include an implant shaping module 630 to shape the implant 635 according to the specification 625. The implant specification 625 may also specify the one or more selections received by the reception module 610. In one embodiment, the determination module 620 and the shaping module 630 are configured to interoperate to form the implant 635. For example, a CNC or similar machine may be programmed to receive measurements 611 or images of teeth or tooth sockets and reproduce shapes of the specific teeth, including roots.

In various embodiments, the dental implant supply system 600 includes a shaping module 630 configured to form or shape the implant 635. The shape module may include various tools or implements configured to add, remove, mold, or modify implant materials to shape the implant 635. For example, the tools or implements may include drills, saws, cutters, lathes, molds, thermal devices, routers, pressure manipulation devices, etc., configured to shape the implant 635. In some embodiments, all or a portion of the shape module includes manually operated tools to hand make implants 635 according to specifications received from the implant determination module 620. For example, selected implant materials may be positioned in a mold according to specifications to form the implant 635, which may comprise the final implant shape or may be further tooled or machined to form the final implant shape. In one embodiment, the shaping module 630 is configured to form the implant 635 from biocompatible material comprising at least one of a hydrogel and a metal. The shaping module 630 may be configured to shape the implant 635 from an allograft or xenograft preparation comprising compact cancellous or cortical bone. The shaping module 630 may be configured to form surface features on an outer surface of the implant 635, wherein the surface features comprise one or more perforations, threads, grooves, and smooth contours. In various embodiments, shape module includes a computer operated machine that may include various cutting implements used to cut, drill, mold, forge, or otherwise shape the implant 635. In general, such a computer operated machine comprises a computer numerical control (CNC) machine or similar system that comprises a computer implemented system configured for automation of various tools configured to form an implant 635, which in one embodiment comprises forming a mold comprising a negative pattern from the measurements 611 or image from which the implant 635 may be molded or cast. In one embodiment, the shaping module 630 comprises a storage medium and logic controller such as one or more electronic processors. The storage medium is configured to store a computer readable file or instructions such as a program that may be executed by the processor to operate the tools according to commands determined by the program. In various embodiments, the shaping module 630 may be configured to employ or include the implant determination program. For example, in one embodiment, the shaping module 630 comprises a CNC machine configured to comprise or have compatibility with manufacturing or design programs such as computer-aided manufacturing or computer-aided design programs, which may include the implant determination module 620. In some embodiments, the CNC system comprises one or a series of phases configured to shape the implant 635 to the desired shape determined by the implant determination program having the at least one anatomical dimension complementary to the tooth socket or root of a tooth socket to be repaired, e.g., reconstituted or obliterated.

In some embodiments, the shaping module 630 may be configured to shape implants 635 including an aperture drilled therein. For example, each specifically prepared implant 635 may include a drilled aperture formed by the shaping module 630. The aperture may be formed in a central portion of the implant 635 and be configured for securing the implant 635 or another implant, such as a tooth implant or prosthesis, to the implant 635. For example, in one embodiment, an aperture may be defined through a top surface of the implant 635 and extend toward a bottom surface. The aperture may be configured to receive a post or otherwise couple to a coupling member. The aperture may stably associate with the coupling member via the aperture. Notably, other points and manners of coupling may be used to retain and thereby stabilize the coupling member, such as clamps, friction fitments, grooves, locks, adhesives, etc. In various embodiments, the coupling member is configured to couple a tooth implant to the graft to thereby retain and stabilize the tooth implant. The aperture may comprise a complementary dimension to the post configured to receive and thereby retain the tooth implant. For example, the tooth implant may include a post configured to engage, e.g., threadably engage, the aperture.

In one embodiment, a kit is provided comprising a plurality of implants 635 comprising grafts comprising a cylindrical conically-shaped plugs having a plurality of different contours. For example, the kit may comprise a first implant 635 having a first contour and a second implant 635 having a second contour wherein the second contour is different than the first.

According to various embodiments, the implants 635 may comprise various synthetic, organic, inorganic, or biological materials. These materials may replace or be in addition to the cancellous or cortical bone. The implants 635 may be dimensioned to fit into a specific tooth socket that may be provided by a user, such as a dentist or medical personal. The implants 635 may be selected from a variety of implants 635 comprising various dimensions from a tissue bank. The implants 635 may be shaped to conform to a dimension of a specific tooth's root. In one embodiment, an implant 635 is made by a CNS or similar device using the measurements 611 or image provided by the user. Shaping the implant 635 may also include forming the graft in a mold or by hand to fit a mold.

According to various embodiments, the system 600 of supplying or manufacturing osseous implants 635 comprising grafts comprises forming a cylindrical plug with the shaping module 630 according to the implant specification 625. Forming may comprise forming grooves, threads, or screw patterns along the body of the plug, e.g., along a side or outer surface portion configured to engage tissue at the implant site. In one embodiment, forming may comprise perforating the plug. For example, perforations may be formed perpendicular, parallel or at an angle with respect to a vertical or longitudinal axis of the plug.

In various embodiments, the system 600 includes a treatment and conditioning module 640. The treatment and conditioning module 640 may be configured to condition or treat the implant 635, for example, by impregnation or application of a coating, after being shaped. The treatment and conditioning module 640 may be configured to treat or condition the implant 635, wherein the treatment comprises at least one of impregnation with an anti-infection agent, impregnation with stem cells, and application of a coating with a flexible and pliable collagen membrane. Notably, it is contemplated that the treatment and conditioning module 640 may be configured to condition or treat the implant 635 or one or more of the implant materials prior to shaping, which may be in addition to or instead of conditioning or treating after shaping. Thus, in some embodiments, conditioning and treatment may be pre-formed prior to shipment or delivery of the implant 635. In other embodiments, conditioning or treatment materials may be ordered and shipped with or separate from the implant 635 to allow the user to condition or treat the implant 635 at a desired time, e.g., a time proximate implantation. In various embodiments, the plug may be loaded with stem cells capable of transforming into osteoprogenitor cells. For example, the method may include loading stem cells in perforations configured to be loaded with stem cells. In one embodiment, the outer surface or side portion surface of the implant 635 is coated with or includes a synthetic material. The synthetic material may be configured to be formed as above. In one embodiment, anti-microbials may be loaded into or incorporated with the synthetic material. In one embodiment, the implant 635 comprises a plug formed of synthetic material. According to various embodiments, implants 635 may be configured to prevent or treat infections. For example, in one embodiment, implants 635 are impregnated with an antibiotic, such as tetracycline, anti-microbial, anti-fungal, antiviral, or any other anti-septic compound. In some embodiments, alternatively or in addition to impregnation with anti-septic, microbial contamination of the implant 635 or affected tooth socket, the bucccal surface of the implant 635 may be covered with a flexible and pliable collagen membrane.

The system 600 may further include a delivery module 650 to deliver the implant 635 to the user, wherein the delivery module 650 is configured to deliver the implant 635 as part of kit comprising implantation instruments or additional implants 635 specific additional teeth or sockets.

In various embodiments, a method of supplying an implant configured to repair or repairing a tooth socket, e.g., a tooth socket damaged by loss or extraction of a tooth includes measuring a dimension of the tooth socket or providing an image of the tooth socket. The method may also include preparing an implant comprising a graft using the measured dimension or image such that the graft is configured to be received or retained by the tooth socket. For example, the graft may comprise a pre-shaped dimension for implantation at the tooth socket. The graft may comprise any desired dimension configured to obliterate the tooth socket. In one embodiment, the graft comprises a generally cylindrical implant of cancellous or cortical bone, e.g., in the form of a conical plug. According to various embodiments, the method of supplying dental implants 635 comprises receiving measurements, e.g., imaging, and selecting a suitable osseous implant. Selecting may comprise generating an implant specification comprising, e.g., identifying or defining, the dimension determined from the measurements. Selecting an implant may also comprise selecting a dimension matched to a size and shape of a tooth root corresponding to a tooth socket, wherein the dimension is determined from measurements determined or ascertained from the three-dimensional image of the recipient tooth socket to be repaired or reconstituted. Selecting may further comprise impregnating the implant with stem cells or an anti-infection agent configured to treat or prevent infection. According one embodiment, the method further comprises shaping the implant according to the specification. Shaping may comprise using a CNC machine to shape the implant according to the specification. Shaping may include forming the implant from biocompatible material comprising at least one of a hydrogel and a metal. In one embodiment, shaping comprises forming the implant from compact cancellous bone or cortical bone, wherein the implant comprises an allograft or xenograft. In one further embodiment, the method includes providing the implant to medical personnel for implantation of the implant into the recipient tooth socket. In one embodiment, the implant is specifically prepared and selected for the user to fill a specific tooth socket. In some aspects, the specifically prepared implant is delivered to a dentist to fill the specific anatomically determined recipient tooth socket. Providing, for example, may comprise providing the implant in a kit comprising a plurality of different dental implants 635 wherein each implant comprises a dimension matched to a size and shape of a tooth root corresponding to a respective specific tooth socket.

Methods and Instrumentation for Implantation

In various embodiments, a method of solid osseous repair and reconstitution of a tooth socket comprises obliterating the socket in the mandible or maxilla. The method may also include measuring or preparing an image of a recipient tooth socket for preparation or selection of an implant. In one embodiment, the method includes selecting a specific size or shape-matched implant to the tooth socket. In one embodiment, the method comprises receiving a specific size or image of a tooth socket and preparing an implant having a matched or complementary dimension to match the tooth socket. According to one method, the implant is formed of a hydrogel. In another embodiment, the implant is formed of a metal. The method may also include sending or delivering the implant comprising the matched or complementary dimension to a user for use according to the method. In one embodiment, the method includes inserting the implant into the recipient socket. Inserting the implant may include loading the implant into a delivery device, such as a delivery tube, and facilitating the insertion of the implant, e.g., by hand.

In various embodiments, an instrument for inserting a bone implant into a tooth socket comprises a curved rod. The curved rod may comprise a lock and screw portion. The screw portion may comprise a short portion at an end of the rod. For example, the screw portion may comprise about 5 mm. The screw portion may be inserted into a predrilled hole to allow the user to insert the bone implant into the tooth socket in a precise and controlled fashion. The instrument is configured to obviate a need to grasp the bone implant with forceps and thereby further avoid slippage, undesired rotation, and inadvertent dropping of the implant into the oral cavity or outside the oral cavity.

The matter set forth in the foregoing description and accompanying drawings is offered by way of illustration only and not as a limitation. While the systems, methods, compositions, and devices for bone grafting have been described and illustrated in connection with certain embodiments, many variations and modifications will be evident to those skilled in the art and may be made without departing from the spirit and scope of the disclosure. For example, the systems, methods, compositions, and devices disclosed herein have been identified, adapted to, and designed for medical use including bone grafting. In one form, this disclosed subject matter may be used to improve bone grafting outcomes in animals in veterinary arts as well as in humans. Those having skill in the art will understand upon reading the present disclosure that the subject matter may be applied to additional grafting procedures associated with bone repair and augmentation. The disclosure is thus not to be limited to the precise details of methodology or construction set forth above as such variations and modification are intended to be included within the scope of the disclosure.

What is claimed is:

1. A method comprising:
    decalcifying whole bone by contacting the bone with a decalcifying solution, wherein the bone comprises whole trabecular bone;
    applying force to compress the decalcified whole bone from a first form to a second form, the second form having a conical shape and compressed relative to the first form, wherein the bone is hydrated when compressed;
    drying the decalcified and compressed whole bone while maintaining compression, wherein, when dried, the bone substantially retains the second form, and wherein drying comprises hypothermically dehydrating the bone using hypothermic dehydration; and
    inserting the decalcified, compressed and dried whole bone at a post extraction tooth socket, wherein the decalcified bone in the first form defines empty trabecular spaces that are reduced or obliterated when the decalcified bone is compressed to the second form, and wherein, when rehydrated following insertion at the post extraction tooth socket, the decalcified bone decompresses to obliterate space between the decalcified bone and the tooth socket and the empty trabecular spaces allow vascular ingrowth and reossification.

2. The method of claim 1, wherein the bone comprises a strip of whole trabecular bone.

3. The method of claim 1, wherein the decalcified, compressed and dried bone comprises an allograft configured for human implantation.

4. The method of claim 1, wherein the decalcified, compressed and dried bone comprises an xenograft configured for human implantation.

5. The method of claim 1, wherein the decalcified bone is 20% to 80% decalcified.

6. The method of claim 5, wherein the decalcified bone is 50% to 60% decalcified.

7. The method of claim 1, wherein applying force comprises positioning the decalcified bone in a compression device between a first wall and a second wall such that the decalcified bone is in the second form, and wherein drying comprises drying the decalcified bone while positioned in the compression device.

8. The method of claim 7, wherein the first and second wall define a volume therebetween that is reduced or reduceable with respect to a dimension of the decalcified bone in the first form such that the dimension of the decalcified bone is compressed to the volume reduced or reduceable defined between the first wall and the second wall when the decalcified bone is compressed in the compression device.

9. The method of claim 8, wherein at least one of the first wall or the second wall comprise a perforation configured to allow fluid to be released from the decalcified bone when compressed.

10. The method of claim 7, wherein the compression device defines a cross-section between the first wall and the second wall, and wherein, when dried, the second form comprises a cross-section complementary to the cross-section defined by the compression device.

11. The method of claim 1, further comprising sectioning fresh or dehydrated whole bone prior to decalcifying the bone to obtain strips of whole bone for the compressing and drying.

12. The method of claim 1, wherein contacting comprises positioning the bone in a bath of the decalcifying solution and performing one or more compression assays during the decalcifying and removing the bone from the bath upon determination that the bone has become soft.

13. The method of claim 1, wherein the decalcifying solution comprises at least one of
    1N HCl,
    citric acid 5% to 20% w/v, 0.24M disodium or tetrasodium salts of EDTA in a balanced salt solution, saline, or water neutralized to a pH around 6.8 to 7.2 with NaOH, or a mixture of 5M EDTA and 5M citric acid.

14. A method of treating a post extraction tooth socket, the method comprising inserting a decalcified trabecular whole bone allograft comprising a strip of whole bone dehydrated by hypothermic dehydration or freeze-drying and in a compressed form at a post extraction tooth socket, wherein the compressed form is characterized by a conical shape and reduced or obliterated trabecular spaces compared to both a hydrated uncompressed form and a dehydrated uncompressed form of the decalcified trabecular whole bone and wherein, when rehydrated following insertion at the maxillary or mandibular defect, the allograft decompresses to obliterate space between the tooth socket and the allograft and the empty trabecular spaces allow vascular ingrowth and reossification.

15. The method of claim 14, wherein the dehydrated decalcified trabecular bone is 20% to 80% decalcified.

16. The method of claim 15, wherein the dehydrated decalcified trabecular bone is 50% to 60% decalcified.

* * * * *